United States Patent [19]

Shepherd et al.

[11] Patent Number: 4,536,346

[45] Date of Patent: Aug. 20, 1985

[54] ARALKANAMIDOPHENYL COMPOUNDS

[75] Inventors: Robert G. Shepherd, Selbyville, Del.; Janis Upeslacis, Pomona, N.Y.

[73] Assignee: American Cyanamid Company, Stamford, Conn.

[21] Appl. No.: 492,094

[22] Filed: May 6, 1983

[51] Int. Cl.$^3$ .................. C07C 121/78; C07C 101/44
[52] U.S. Cl. .................. 260/465 D; 560/21; 560/45; 560/47; 560/48; 562/435; 562/455; 562/456; 562/457; 564/86; 564/87; 564/163; 564/166; 564/170; 564/174; 564/181; 564/182
[58] Field of Search .................. 564/182, 181, 86, 87, 564/163, 166, 170, 174; 560/19, 21, 45, 47, 48; 562/433, 435, 455, 456, 457; 260/465 D

[56] References Cited

U.S. PATENT DOCUMENTS 3,835,128  9/1974  Bracha et al. .................. 564/182 X

OTHER PUBLICATIONS

Grummitt et al., J. Am. Chem. Soc., 71, 4156, (1949).

*Primary Examiner*—Dolph H. Torrence
*Attorney, Agent, or Firm*—Edward A. Conroy, Jr.

[57] ABSTRACT

This disclosure describes novel substituted aralkanamidobenzoic acids and analogs thereof. These compounds are useful pharmaceutical agents for ameliorating atherosclerosis by inhibiting the formation and development of atherosclerotic lesions in the arterial wall of mammals.

49 Claims, No Drawings

ARALKANAMIDOPHENYL COMPOUNDS

BACKGROUND OF THE INVENTION

This invention relates to new organic compounds useful as pharmaceutical agents. The novel compounds of the present invention are antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilizaiton of these compounds in the treatment of disease in mammals. Further, the invention contemplates methods for treating atherosclerosis in a manner designed to prevent, arrest, or reverse the course of the disease.

Atherosclerosis is a form of arteriosclerosis characterized by lipid accumulation in and thickening of the arterial walls of both medium- and large-sized arteries. Arterial walls are thereby weakened, and the elasticity and effective internal size of the artery is decreased. Atherosclerosis is the most common cause of coronary artery disease and is of great medical importance since the occlusion of medium- and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plagues has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme "Fatty acyl CoA: cholesterol acyl transferase" or ACAT, and the accumulation and storage of cholesterol esters in the arterial wall is associated with increased levels of this enzyme [Hashimoto and Dayton, Atherosclerosis, 28, 447 (1977)]. In addition, cholesterol esters are removed from the cells at a slower rate than unesterified cholesterol [Bonjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions. The compounds of the present invention are very potent inhibitors of the ACAT enzyme. Thus, these compounds are useful for controlling and normalizing the cholesterol ester content of mammalian arterial walls. In contrast to the serum hypocholesterolemic agents which are well known in the art to merely lower cholesterol in the blood stream, the compounds of this invention decrease the accumulation and storage of the cholesterol in the arterial walls of mammals. Further, the compounds of this invention inhibit the formation or development of atherosclerotic lesions in mammals. The exact mechanism by which these compounds exhibit this antiatherosclerotic activity is not known, and the invention should not be construed as limited to any particular mechanism of antiatherosclerotic action.

SUMMARY OF THE INVENTION

This invention relates to new organic compounds and more particularly is concerned with aralkanamidobenzoic acids and analogs thereof which may be represented by the following structural formula:

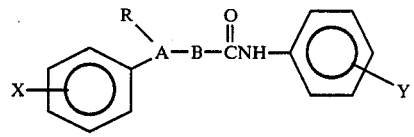

wherein A is selected from the group consisting of:

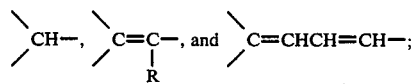

B is selected from the group consisting of a chemical bond and, when A is >CH—, also from an optionally branched or unbranched $C_1$–$C_4$ alkylene group; R is selected from the group consisting of hydrogen, $C_1$–$C_4$ alkyl, phenyl, and phenyl substituted with X; X represents one or more substituents independently selected from the group consisting of hydrogen, $C_1$–$C_4$ alkyl, hydroxy, $C_1$–$C_4$ alkoxy, halo, and nitro; Y represents one or more substituents independently selected from the group consisting of hydrogen, $C_1$–$C_4$ alkyl, hydroxy, $C_1$–$C_4$ alkoxy, halo, trifluoromethyl, nitro, amino, acetamido, acetyl, formyl, cyano, carboxy, $C_1$–$C_4$ carboalkoxy, carboxamido, sulfonamido, $—CO_2CH_2CO_2C_2H_5$, $—CO_2CH_2CO_2CH_3$, and $—CO_2CH_2CO_2H$; and the pharmaceutically-acceptable salts thereof.

Preferred embodiments of the invention relate to those compounds wherein A and B taken together represent two carbon atoms joined by either a single or double bond: that is, A is >CH— and B is —$CH_2$— or A is >C—CH— and B is a chemical bond. Of these, the more preferred are the compounds wherein R is phenyl substituted with X, and X is chloro, methyl, or methoxy. Of the latter, the most preferred are those compounds wherein Y is hydrogen, carboalkoxy, carboxy, or an alkali metal salt thereof.

Representative specific embodiments involve, for example, 4-[3,3-bis-(p-chlorophenyl)propionamido]benzoic acid; 4-[3,3-bis-(p-tolyl)propionamido]benzoic acid; 4-[3,3-bis-(p-methoxyphenyl)propionamido]benzoic acid; ethyl 4-[3,3-bis-(p-chlorophenyl)propionamido]benzoate; ethyl 4-[3,3-bis-(p-tolyl)propionamido]benzoate; ethyl 4-[3,3-bis-(p-methoxyphenyl)propionamido]benzoate; sodium 4-[3,3-bis-(p-chlorophenyl)propionamido]benzoate; sodium 4-[3,3-bis-(p-tolyl)propionamido]benzoate; sodium[3,3-bis-(p-methoxyphenyl)propionamido]benzoate; 4-[3,3-bis-(p-chlorophenyl)-acrylamido]benzoic acid; 4-[3,3-bis-(p-chlorophenyl)acrylamido]benzoate; 4-[3,3-bis-(p-tolyl)acrylamido]benzoate; ethyl 4-[3,3-bis-(p-methoxyphenyl)acrylamido]benzoate; 3,3-bis-(p-chlorophenyl)acrylanilide; 3,3-bis-(p-tolyl)acrylanilide; 3,3-bis-(p-methoxyphenyl)acrylanilide; 3,3-bis-(p-chlorophenyl)propionanilide; 3,3-bis-(p-tolyl)propionanilide; 3,3-bis-(p-methoxyphenyl)propionanilide. Additional specific embodiments include the compounds of Examples 47-58, 60-66, and 68-73.

With reference to the above formula, the invention contemplates as novel compounds per se only those analogs wherein Y is not hydrogen or chloro, A is >CH—, and B is a chemical bond; since two of the compounds of this class are known in the art. Although bis-(p-chlorophenyl)acetanilide and bis-(p-chlorophenyl)aceto-4-chloroanilide are known —O. Grummitt and D. Marsh, J. Am. Chem. Soc., 71, 4156 (1949)—no specific use is reported for either.

This invention also relates to a method of reducing the cholesterol ester content of an arterial wall in a mammal in need of such treatment which comprises administering to said mammal a cholesterol ester-reducing amount of a compound as recited above.

This invention further relates to a method of inhibiting atherosclerotic lesion development in a mammal in need of such treatment which comprises administering to said mammal an atherosclerotic lesion development-inhibiting amount of a compound as recited above.

This invention still further relates to a pharmaceutical composition suitable for reducing the cholesterol ester content of an arterial wall in a mammal in need of such treatment which comprises a cholesterol ester-reducing amount of a compound as recited above and a non-toxic, pharmaceutically-acceptable carrier.

Further still, this invention relates to a pharmaceutical composition suitable for inhibiting atherosclerotic lesion development in a mammal in need of such treatment which comprises an atherosclerotic lesion development-inhibiting amount of a compound as recited above and a non-toxic, pharmaceutically-acceptable carrier.

Finally, this invention relates to a process for preparing compounds as recited above which comprises reacting an acid derivative of the formula:

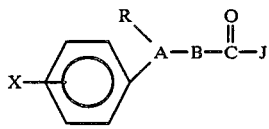

with an aniline of the formula:

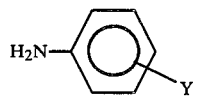

or reacting a carbonyl compound of the formula:

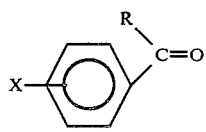

with a phosphonate ester of the formula:

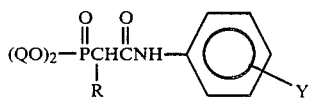

wherein R, X, A, B, and Y are as defined hereinabove; J is selected from the group consisting of halo, $C_1$-$C_4$ alkoxy, and $C_1$-$C_4$ alkanoyloxy; and Q is selected from the group consisting of $C_1$-$C_4$ alkyl and phenyl.

DETAILED DESCRIPTION OF THE INVENTION

Many of the compounds of this invention are prepared by reactions of aralkanoyl or aralkenoyl halides with substituted anilines, for example, treatment of 3,3-bis-(p-chlorophenyl)acryloxy chloride with ethyl 4-aminobenzoate yields ethyl 4-[3,3-bis-(p-chlorophenyl)acrylamido]benzoate. Often these reactions are conducted at or below room temperature; however, in certain cases elevated temperatures are required. These reactions may be carried with or without an added acid acceptor, such as triethylamine, using organic solvents such as dichloromethane, chloroform, or tetrahydrofuran. Certain of the products of this type of reaction may be further transformed to yield other compounds of the invention. Examples of such further transformations are the alkaline hydrolysis of ethyl 4-[3,3p-bis-(p-chlorophenyl)acrylamido]benzoate which yields 4-[3,3-bis-(p-chlorophenyl)acrylamido]benzoic acid and the catalytic hydrogenation of ethyl 4-[3,3-bis-(p-chlorophenyl)acrylamido]benzoate which yields ethyl 4-[3,3-bis-(p-chlorophenyl)propionamido]benzoate.

Many of the aralkanoyl and aralkenoyl halides required for the above-described reacitons were not previously known. Their preparation is accomplished by a variety of methods. Certain aralkenoyl halides are obtained by the Wadsworth-Emmons reaction of triethylphosphonoacetate with a benzophenone followed by alkaline hydrolysis and acid halide formation. These Wadsworth-Emmons are conducted at temperatures from 0° C. to 50° C. in ether solvents such tetrahydrofuran or 1,2-dimethoxyethane for periods of 1 to 25 hours. An example of this sequence of reactions is the Wadsworth-Emmons reaction of triethylphosphonoacetate with 4,4'-dichlorobenzophenone which yields ethyl 3,3-bis-(p-chlorophenyl)acrylate. Hydrolysis of this acrylate ester with sodium hydroxide affords 3,3-bis-(p-chlorophenyl)acrylic acid. Treatment of this acrylic acid with thionyl chloride yields 3,3-bis-(p-chlorophenyl)acryloyl chloride. Aralkanoyl halides corresponding to the aralkenoyl halides may be obtained by catalytic hydrogenation of the intermediate acrylate esters or acrylic acids followed by transformations similar to those just described for these esters and acids. Thus, catalytic hydrogenation of ethyl 3,3-bis-(p-chlorophenyl)acrylate followed by alkaline hydrolysis and acid halide formation affords 3,3-bis-(p-chlorophenyl)propionyl chloride. Similarly, catalytic hydrogenation of 3,3-bis-(p-chlorophenyl)acrylic acid followed by treatment with thionyl chloride yields 3,3-bis-(p-chlorophenyl)propionyl chloride.

Other methods useful for the synthesis of aralkanoic and aralkenoic acid intermediates are, first, alkylation of benzophenones with dianions derived from alkanoic acids followed by dehydration and, if required, catalytic hydrogenation. An example of the preparation of both an aralkenoic and an aralkanoic acid by this method is the reaction of 4,4'-dimethylbenzophenone with the dianion of acetic acid to yield 3-hydroxy-3,3-bis(p-tolyl)acrylic acid. Further, catalytic hydrogenation of this acid affords the corresponding aralkanoic acid, 3,3-bis-(p-tolyl)propionic acid. A second method useful for the preparation of certain aralkanoic acids is the Friedel- Crafts alkylation of activated aromatic compounds. An example is the reaction of anisole with 4-methoxycinnamic acid to yield bis-3,3-(p-methoxyphenyl)-propionic acid.

Certain of the compounds of this invention are prepared directly by the reaction of substituted diethyl phosphonoacetanilides with benzophenones. The requisite substituted diethyl phonsphonoacetanilides are prepared as follows. Treatment of bromoacetyl bromide with a substituted aniline yields a substituted bromoacetanilide. Reaction of the bromoacetanilide with triethylphosphite affords the substituted diethyl phosphonoacetanilide required for reaction with a benzophone. An example of this series of reactions is the acylation of ethyl 4-aminobenzoate to yield ethyl 4-bromoacet anilide followed by reaction with triethyl phosphite to yield ethyl 4-[(diethylphosphono)acetamido]benzoate. Reaction of this diethylphosphonoacetanilide with 4,4'-diethylbenzophenone then affords ethyl 4-[3,3-bis-(p-tolyl)acrylamido]benzoate directly. If the saturated analog is desired, catalytic hydrogenation of this ester may be used to obtain ethyl 4-[3,3-bis-(p-tolyl)propionamido]benzoate.

The compounds of the present invention are generally obtained as crystalline solids having characteristic melting points and spectra. They are appreciably soluble in many organic solvents but are generally less soluble in water. Those compounds which are carboxylic acids may be converted to their alkali metal and alkaline earth salts by treatment with appropriate metal hydroxides, and these salts exhibit increased water solubility.

The preparation and properties of the compounds of this invention will be described in greater detail in conjunction with the specific examples shown below.

The compounds of the present invention were tested for their ability to inhibit the enzymatic esterification of cholesterol according to the following procedure:

Rat adrenals were homogenized in 0.2M monobasic potassium phosphate buffer, pH 7.4, and centrifuged at 1,000 times gravity for 15 minutes at 5° C. The supernatant, containing the microsomal fraction, served as the source of the cholesterol-esterifying enzyme, fatty acyl CoA: cholesterol acyl transferase (ACAT). A mixture comprising 50 parts of adrenal supernatant, 10 parts of albumin (BSA) (50 mg./ml.), 20 parts of oleoyl CoA ($^{14}$C-0.4 μCi), 3 parts of test compound, and 500 parts of buffer was pre-incubated at 37° C. for 10 minutes. After treatment with 20 parts of oleoyl CoA ($^{14}$C-0.4 μCi), the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesterol ester fraction was counted in a scintillation counter. This procedure is a modification of that described by Hashimoto, et al., Life Scie., 12 (Part II), 1–12 (1973).

The results of this test on representative compounds of this invention appear in Table I. The final concentration of the test compound was 5.2 μg./ml., and the effectiveness of the compound is expressed as percent inhibition of the ACAT enzyme compared to control values.

TABLE I

| COMPOUND | % INHIBITION |
| --- | --- |
| 4-(p-Chlorocinnamamido)benzoic acid, ethyl ester | 51 |
| 4-(p-chlorocinnamamido)benzoic acid | 41 |
| 4-(p-Chlorohydrocinnamamido)benzoic acid, ethyl ester | 30 |
| 4-(p-Chlorohydrocinnamamido)benzoic acid | 33 |
| 4-[3,3-Bis(p-chlorophenyl)acrylamido]benzoic acid | 91 |
| 4-[3,3-Bis(p-chlorophenyl)propionamido]benzoic acid, ethyl ester | 94 |
| 4-[3,3-Bis(p-chlorophenyl)acrylamido]benzoic acid, ethyl ester | 93 |
| 4-[3,3-Bis(p-chlorophenyl)propionamido]benzoic acid | 71 |
| 4-(p-Methylhydrocinnamamido)benzoic acid, ethyl ester | 25 |
| 4-(p-Methoxyhydrocinnamamido)benzoic acid, ethyl ester | 28 |
| 4-(p-Methoxycinnamamido)benzoic acid, ethyl ester | 53 |
| 4-(p-Methoxycinnamamido)benzoic acid | 20 |
| 4-(p-Chlorophenyl)hexanamidobenzoic acid | 18 |
| 3-[3,3-Bis(p-chlorophenyl)acrylamido]benzoic acid, methyl ester | 94 |
| 2-[3,3-Bis(p-chlorophenyl)acrylamido]benzoic acid, methyl ester | 71 |
| 3-[3,3-Bis(p-chlorophenyl)acrylamido]benzoic acid | 98 |
| 2-[3,3-Bis(p-chlorophenyl)acrylamido]benzoic acid | 32 |
| 4-[3,3-Bis(p-chlorophenyl)acrylamido]benzoic acid, ethyl glycolate ester | 88 |
| 4-(p-chloro-β-phenylcinnamamido)benzoic acid, ethyl ester | 92 |
| 4-[3,3-Bis(p-fluorophenyl)acrylamido]benzoic acid, ethyl ester | 74 |
| 4-[3,3-Bis(p-fluorophenyl)acrylamido]benzoic acid | 79 |
| 4-(p-Chloro-β-phenylcinnamamido)benzoic acid | 77 |
| 4-(3,3-Diphenylacrylamido)benzoic acid | 66 |
| 4-(3,3-Diphenylacrylamido)benzoic acid, ethyl ester | 40 |
| 4-[3,3-Di-(p-tolyl)acrylamido]benzoic acid, ethyl ester | 97 |
| 4-(p-Methyl-β-phenylcinnamamido)benzoic acid, ethyl ester | 88 |
| 4-(p-Methyl-β-phenylcinnamamido)benzoic acid | 80 |
| 4-(p-Chloro-β-methylcinnamamido)benzoic acid, ethyl ester | 74 |
| 4-(p-Chloro-β-methylcinnamamido)benzoic acid | 71 |
| 4-[3,3-Di-(p-tolyl)acrylamido]benzoic acid | 89 |
| 3,3-Bis(p-chlorophenyl)-4'-cyanoacrylanilide | 96 |
| 4'-Acetyl-3,3-bis(p-chlorophenyl)acrylanilide | 86 |
| 4-[3,3-Bis(p-methoxyphenyl)acrylamido]benzoic acid | 78 |
| 4-(3,4-Dichlorophenyl-β-methylacrylamido)benzoic acid, ethyl ester | 74 |
| 4-[3,3-Bis(p-methoxyphenyl)acrylamido]benzoic acid, ethyl ester | 97 |
| 4-[3,3-Bis(p-bromophenyl)acrylamido]benzoic acid, ethyl ester | 96 |
| 4-[3,3-Bis(p-bromophenyl)acrylamido]benzoic acid | 90 |
| 4-(4-Chloro-3-nitro-β-phenylcinnamamido)benzoic acid, ethyl ester | 94 |
| 4-[2,2-Bis-(p-chlorophenyl)acetamido]benzoic acid, ethyl ester | 86 |
| 4-[2,2-Bis-(p-chlorophenyl)acetamido]benzoic acid | 71 |
| 4-[6-(p-chlorophenyl)hexanamido]benzoic acid, ethyl ester | 42 |
| N—Phenyl-3,3-bis(4-methoxyphenyl)propionamide | 91 |
| N—(p-Chlorophenyl)-3,3-bis(4-methoxyphenyl)propionamide | 91 |
| N—(p-Bromophenyl)-3,3-bis(4-methoxyphenyl)propionamide | 79 |
| N—(p-Fluorophenyl)-3,3-bis(4-methoxyphenyl)propionamide | 92 |
| N—(p-Nitrophenyl)-3,3-bis(4-methoxyphenyl)propionamide | 94 |
| N—(p-Tolyl)-3,3-bis(4-methoxyphenyl)propion- | 97 |

TABLE I-continued

| COMPOUND | % INHIBITION |
|---|---|
| N—(p-Methoxyphenyl)-3,3-bis(4-methoxyphenyl)propionamide | 58 |
| N—(p-Cyanophenyl)-3,3-bis(4-methoxyphenyl)propionamide | 94 |
| N—(p-Trifluromethylphenyl)-3,3-bis(4-methoxyphenyl)propionamide | 92 |
| N—(p-Acetylphenyl)-3,3-bis(4-methoxyphenyl)propionamide | 82 |
| N—(p-Carboethoxyphenyl)-3,3-bis(4-methoxyphenyl)propionamide | 91 |
| N—(p-Carboxyphenyl)-3,3-bis(4-methoxyphenyl)propionamide | 45 |
| N—Phenyl-3,3-bis(p-tolyl)propionamide | 82 |
| N-(p-Chlorophenyl)-3,3-bis(p-tolyl)propionamide | 89 |
| N—(p-Fluorophenyl)-3,3-bis(p-tolyl)propionamide | 92 |
| N—(p-Cyanophenyl)-3,3-bis(p-tolyl)propionamide | 90 |
| N—(p-Tolyl)-3,3-bis(p-tolyl)propionamide | 66 |
| N—(p-Carboethoxyphenyl)-3,3-bis(p-tolyl)propionamide | 95 |
| N—(p-Trifluoromethylphenyl)-3,3-bis(p-tolyl)propionamide | 94 |
| N—Phenyl-3,3-bis(p-chlorophenyl)propionamide | 50 |
| N—(p-Fluorophenyl)-3,3-bis(p-chlorophenyl)propionamide | 67 |
| N—(p-Tolyl)-3,3-bis(p-chlorophenyl)propionamide | 36 |
| N—(p-Cyanophenyl)-3,3-bis(p-chlorophenyl)propionamide | 96 |
| N—(p-Acetylphenyl)-3,3-bis(p-chlorophenyl)propionamide | 95 |
| N—(p-Trifluoromethylphenyl)-3,3-bis(p-chlorophenyl)propionamide | 35 |

When the compounds are employed for the above utility, they may be combined with one or more pharmaceutically-acceptable carriers, e.g., solvents, diluents, and the like, and may be administered orally in such forms as tablets, capsules, dispersible powders, granules, suspensions containing, for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 05up to about 00% of the active ingredient in combination with the carrier, more usually between 5% and 60% by weight.

The antiathermosclerotic effective dosge of active ingredient employed for the reduction of cholesterol ester content in the arterial walls of a mammal may vary depending on the particular compound employed, the mode of administration, and the severity of the condition being treated. In general, however, satisfactory results are obtained when the compounds of the invention are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams, preferably from about 100 milligrams to 2,000 milligrams. Dosage forms suitable for internal use comprise from about 25 to 2,500 milligrams of the active compound in intimate admixture with a solid or liquid pharmaceutically-acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include sterile water, polyethylene glycols, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT, and BHA.

The preferred pharmaceutical composition from the stand-point of ease of preparation and administration are solid compositions, particularly tablets and hard-filled or liquid-filled capsules. Oral administration of Compound I is preferred.

These active compounds may also be administered parenterally or intraperitoneally. Solutions or suspensions of these active compounds as a free base or pharmacologically-acceptable salt can be prepared in water suitably mixed with a surfactant such as hydroxypropyl-cellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol,, and liquid polyethylene glycol), suitable mixtures thereof, and vegetable oils.

EXAMPLE 1

4-(p-Chlorocinnamamido)benzoic acid, ethyl ester

To a solution of 20 g. of p-chlorocinnamic acid in 200 ml. of benzene is added dropwise 43 g. of thionyl chloride. The solution is refluxed for 5 hours, cooled, and evaporated. The residue is dissolved in benzene, and the solution evaporated to yield 21.8 g. of p-chlorocinnamoyl chloride.

The 21.8 g. of p-chlorocinnamoyl chloride is dissolved in 250 ml. of dichloromethane. To this is added, with stirring, a solution of 35.7 g. of ethyl 4-aminobenzoate in 250 ml. of dichlormethane. The mixture is stirred overnight, then 300 ml. of water are added, stirring is continued for 30 minutes, and the solid is collected by filtration and dried. This solid is boiled in 600 ml. of ethanol and 100 ml. of chloroform, filtered, and the volume reduced to 450 ml., giving a solid, 15.0 g. of which is recrystallized from a mixture of 800 ml. of ethanol and 250 ml. of chloroform by boiling to a volume of 250 ml., giving 13.57 g. of the desired product as off-white crystals, m.p. 203°–204° C.

EXAMPLE 2

4-(p-Chlorocinnamamido)benzoic acid

A solution of 7.1 g. of p-(p-chlorocinnamamido)benzoic acid, ethyl ester and 1.6 g. of potassium hydroxide in 50 ml. of 95% ethanol is stirred at 75° C. overnight. A 25 ml. portion of water and 200 mg. of potassium hydroxide are added, and stirring is continued at 75° C. for 1.5 hours. The mixture is then diluted with 150 ml. of water, adjusted to pH 3 with 37% hydrochloric acid, and the precipitate is collected and dried. The solid is boiled in 100 ml. of methyl cellosolve, cooled, and the solid is collected, washed with ethanol, and dried, giving 5.51 g. of the desired product as a white powder, m.p. 333°–336° C. (dec.).

EXAMPLE 3

4-(p-Chlorohydrocinnamamido)benzoic acid, ethyl ester

A mixture of 30.0 g. of 4-(p-chlorocinnamamido)benzoic acid, ethyl ester, 500 mg. of 10% palladium on carbon, and 150 ml. of tetrahydrofuran is hydrogenated in a Parr apparatus, over a 2 hour period, repressurizing until hydrogen uptake is complete. The mixture is filtered, and the filtrate is evaporated. The solid is crystallized from 175 ml. of ethanol, giving 26.8 g. of the desired product as white crystals, m.p. 163°–165° C.

EXAMPLE 4

4-[3,3-Bis(p-chlorophenyl)acrylamido]benzoic acid, ethyl ester

A solution of 48.52 g. of bis-$\beta,\beta$-(p-chlorophenyl)acrylic acid and 60 g. of thionyl chloride in 250 ml. of benzene is stirred at reflux for 4 hours. The solution is cooled and then evaporated. The residue is dissolved in benzene and the solution evaporated to yield 41.8 g. of bis-$\beta,\beta$-(p-chlorophenyl)acryloyl chloride.

This 41.8 g. of bis-$\beta,\beta$-(p-chlorophenyl)acryloyl chloride is dissolved in 250 ml. of dichloromethane, and to the stirred solution is slowly added a mixture of 24.3 g. of benzocaine and 14.8 g. of triethylamine in 250 ml. of dichloromethane. This mixture is stirred for 2 hours, then refluxed for one hour, cooled and washed with 300 ml. of 10% hydrochloric acid. The acid wash is in turn washed with 100 ml. of dichloromethane. The combined organic layers are washed with 100 ml. of brine and evaporated. The residue is boiled in 250 ml. of ethanol, then 200 ml. of chloroform are added, the solution is filtered, and the filtrate is boiled down to a volume of 250 ml. The resulting solid is washed with 400 ml. of ethanol, and 6 g. is recrystallized from 50 ml. of acetone, giving 4.89 g. of the desired product as white crystals, m.p. 207°–209° C.

EXAMPLE 5

4-(p-Methylhydrocinnamamido)benzoic acid, ethyl ester

A solution of 65 g. of p-methylcinnamic acid, 1 g. of palladium on carbon catalyst, and 200 ml. of tetrahydrofuran is hydrogenated in a Parr apparatus at an initial pressure of 50 p.s.i., overnight. The mixture is filtered and the filtrate is evaporated, giving 65.2 g. of 3-(4-methylphenyl)propionic acid.

A solution of 27 g. of 3-(4-methylphenyl)propionic acid and 58.7 g. of thionyl chloride in 550 ml. of benzene is refluxed for 5 hours. The benzene is evaporated, and the residue is recrystallized form benzene, giving 29.8 g. of 3-(4-methylphenyl)propionyl chloride.

A solution of 15 g. of 3-(4-methylphenyl)propionyl chloride in 100 ml. of dichloromethane is created with stirring with a solution of 15 g. of benzocaine and 9.13 g. of triethylamine in 100 ml. of dichloromethane. The mixture is stirred overnight, then washed with 100 ml. each of 10% hydrochloric acid, water, and brine, then dried with magnesium sulfate, and evaporated to yield a solid. This solid is crystallized from 200 ml. of acetonitrile and dried in vacuo, giving 22.08 g. of the desired product, m.p. 154°–155° C.

EXAMPLE 6

4-(p-Methoxyhydrocinnamamido)benzoic acid, ethyl ester

A solution of 27.4 g. of p-methoxyhydrocinnamic acid and 59.7 g. of thionyl chloride in 550 ml. of benzene is refluxed for 5 hours, then cooled, and evaporated. The residue is dissolved in benzene and the solution evaporated to yield 30.0 g. of p-methoxyhydrocinnamoyl chloride.

A solution of 13.73 g. of benzocaine and 11.56 ml. of triethylamine in 100 ml. of ether is slowly added to a stirred solution of 15 g. of p-methoxyhydrocinnamoyl chloride in 100 ml. of ether. The mixture is stirred overnight, 250 ml. of dichloromethane are added, and the mixture is extracted with 200 ml. of water, then 200 ml. of 10% hydrochloric acid, dried over magnesium sulfate, and evaporated to yield a solid. This solid is crystallized from 200 ml. of toluene, giving 21.4 g. of the desired product as white crystals, m.p. 134°–135.5° C.

EXAMPLE 7

4-(p-Methoxycinnamamido)benzoic acid, ethyl ester

A solution of 30 g. of p-methoxycinnamic acid and 66.1 g. of thionyl chloride in 550 ml. of benzene is refluxed for 5 hours. The solvent is evaporated, and the residue is dissolved in benzene and the solution evaported to yield 33.09 g. of p-methoxycinnamoyl chloride.

To a solution of 10 g. of p-methoxycinnamoyl chloride in 200 ml. of dichloromethane is slowly added a solution of 0.24 g. of benzocaine and 7.1 ml. of triethylamine in 200 ml. of dichloromethane. The mixture is stirred for 19 hours, then the organic layer is washed with 200 ml. of 10% hydrochloric acid followed by 200 ml. of brine, dried over magnesium sulfate, and condensed to a solid. This solid is crystallized from 100 ml. of ethanol, giving 10.6 g. of the desired product as yellow crystals, m.p. 163°–165.5° C.

EXAMPLE 9

4-[3,3-Bis(p-chlorophenyl)acrylamido]benzoic acid, sodium salt

A mixture of 19.1 g. of 50% sodium hydride in oil dispersion in 2.2 liters of diethyl ether is stirred in a cold water bath, and 89.3 g. of 4-(2-phosphonoacetamido)benzoic acid, triethy ester are added in portions (exothermic). The solution is stirred for ½ hour, 100 g. of 4,4'-dichlorobenzophenone are added, and the mixture is stirred overnight. The solution is decanted form the brown oil and residue, evaporated to near dryness, and saved. The brown residue is stirred vigorously with 500 ml. of dichloromethane. The above residue after evaporation is boiled briefly with 500 ml. of dichlormethane.

Both organic solutions are decanted, combined, washed with water, then brine, and evaporated to yield a solid. This solid is dissolved in 1 liter of dichloromethane, filtered, and extracted with two 250 ml. portions of water. The solution is dried and evaporated to yield 125.1 g. of bis(4-chlorophenyl)acrylic acid, ethyl ester.

The above ester is dissolved in 800 ml. of ethanol and 80 ml. of water, and 29 g. of potassium hydroxide are added. The solution is refluxed for one hour, cooled, and avaporated to a residue which is dissolved in 2 liters of water, filtered through celite, and adjusted to pH 2 with concentrated sulfuric acid. The mixture is added to 1 liter of boiling dichloromethane. The dichloromethane layer is separated, dried white hot, filtered, and evaporated, giving 98.0 g. of bis(4-chlorophenyl)acrylic acid.

A 105.6 g. portion of bis(4-chlorophenyl)acrylic acid is added to 800 ml. of toluene. A 140 ml. portion of thionyl chloride is added over a 5 minute period, and the mixture is stirred at 80° C. for 5 hours. The toluene is evaporated, and the residue is dissolved in toluene, and the solution is evaporated to yield 121.0 g. of bis(4-chlorophenyl)acryloyl chloride.

A solution of 15 g. of bis(4-chlorophenyl)acryloyl chloride in 100 ml. of tetrahydrofuran is cautiously added to a solution of 30 g. of benzocaine in 400 ml. of tetrahydrofuran and stirred for 48 hours. The reaction is diluted with 1 liter of water. The resulting oil is decanted, and the water layer is extracted with two 200 ml. portions of dichloromethane. The combined oil and extracts are washed with 200 ml. of 10% hydrochloric acid. The dichloromethane layer is separated, dried over magnesium sulfate, and evaporated to yield a solid. This solid is crystallized from 500 ml. of acetic acid, giving 15.0 g. of 4-[3,3-bis(p-chlorophenyl)acrylamido]benzoic acid.

dTo a hot solution of 10 g. of 4-[3,3-bis(p-chlorophenyl)acrylamido]benzoic acid in 300 ml. of alcohol is added 5 ml. of 10N sodium hydroxide solution. The mixture is cooled, the precipitate is collected, washed with ethanol, and dried in vacuo, giving 9.75 g. of the desired product as a yellow powder, m.p. 365°-370° C. (dec.).

EXAMPLE 9

3-[3,3-Bis(p-chlorophenyl)acrylamido]benzoic acid, methyl ester

A solution of 20.0 g. of bis(4-chlorophenyl)acryloyl chloride in 150 ml. of dichloromethane is added to a stirred solution of 10.3 g. of methyl 3-aminobenzoate and 12.2 ml. of triethylamine in 150 ml. of dichloromethane. This solution is stirred under reflux for 3 hours and then at room temperature overnight and evaporated. The residue is stirred with 300 ml. of boiling acetone, filtered white hot, and the filtrate is chilled. The resulting solid is collected and dried in vacuo, giving 13.8 g. of the desired product as a white solid, m.p. 155°-159° C.

EXAMPLE 10

2-[3,3-Bis(p-chlorophenyl)acrylamido]benzoic acid, methyl ester

A solution of 20.0 g. of bis(4-chlorophenyl)acryloyl chloride in 150 m. of dichloromethane is added to a stirred solution of 10.3 g. of methyl 2-aminobenzoate and 12.2 ml. of triethylamine in 150 ml. of dichloromethane. This solution is stirred under reflux for 3 hours, then overnight at room temperature, and evaporated. The residue is stirred with 300 ml. of boiliing acetone, filtered white hot, and chilled. The resulting solid is collected and dried in vacuo, giving 15.6 g. of the desired product as a white solid, m.p. 141°-143° C.

EXAMPLE 11

4-[p-Chloro-$\beta$-(p-chlorophenyl)cinnamamido]benzoic acid, ethyl glycolate ester A slurry of 13.03 g. of 4-[3,3-bis(p-chlorophenyl)acrylamido]benzoic acid, sodium salt, 14.7 g. of ethyl chloroacetate, and 50 ml. of hexamethylphosphortriamid is heated at 75° C. for 16 hours. The mixture is diluted with 50 ml. of water and cooled to 2° C. The resulting solid is collected, washed with water, dried, and recrystallized from a mixture of 130 ml. of toluene and 20 ml. of hexane, giving 7.3 g. of the desired product as a white solid.

Similarly prepared from methyl chloroacetate is 4-[p-chloro-$\beta$-(p-chlorophenyl)cinnamido]benzoic acid, methyl glycolate ester. Alkaline hydrolysis of the latter affords 4-[p-chloro-$\beta$-(p-chlorophenyl)cinnamido]benzoic acid.

EXAMPLE 12

4-(p-Chloro-$\beta$-phenylcinnamamido)benzoic acid, ethyl ester

A solution of 96 ml. of bromoacetyl bromide in 800 ml. of dichloromethane is added, during one hour, to a stirred solution of 165 g. of ethyl 4-aminobenzoate and 165 ml. of triethylamine in 1 liter of dichloromethane white maintaining the temperature at 0° C. The solution is then stirred at room temperature for 20 hours and the extracted with water, dried, and evaporated. The residue is crystallized from 2 liters of toluene and dried, giving 223 g. of 4-(bromoacetamido)benzoic acid, ethyl ester.

A mixture of 146 g. of the above ester, 230 ml. of triethylphosphite, and 800 ml. of toluene is stirred and heated at 105°-110° C. for 2 hours, then cooled, and the solvent is evaporated at 50° C. The residue is reevaporated three times from 400 ml. of hexane. The solid is triturated with 300 ml. of hexane and air dried, giving 170 g. of 4-(2-phosphonoacetamido)benzoic acid, triethyl ester.

To a suspension of 2.04 g. of sodium hydride [(50% suspension in oil) washed with 30 ml. of hexane] in 70 ml. of dry dimethoxyethane is added portionwise 8.6 g. of 4-(2-phosphonoacetamido)benzoic acid triethyl ester over 2 minutes. The mixture is stirred for 20 minutes, then 5.42 g. of 4-chlorobenzophenone is added. This mixture is refluxed for 3½ hours, cooled, and 300 ml. of water are added. The mixture is extracted with two 150 ml. portions of dichloromethane. The organic extracts are stripped to dryness. The residue is dissolved in acetone, then hexane is added to turbidity. The solid is collected, washed with hexane, dissolved in 15 ml. of hot acetonitrile and filtered. The filtrate is refrigerated, and the resulting solid is collected, washed with hexane, and dried, giving 820 mg. of the desired product as a white solid, m.p. 173°-175° C.

EXAMPLE 13

4-[3,3-Bis(p-fluorophenyl)acrylamido]benzoic acid, ethyl ester

To a suspension of 3.28 g. of sodium hydride [(50% in oil) washed with 2×40 ml. of hexane] in 30 ml. of dimethylformamide is added dropwise a solution of 6.86 g. of 4-(2-phosphonoacetamido)benzoic acid, triethyl ester in 30 ml. of dimethylformamide. The mixture is stirred for 20 minutes, then 4.36 g. of 4,4'-difluorobenzophenone are added, and stirring is continued for one hour. The mixture is then heated at 60°–70° C. for one hour, cooled, and 200 ml. of water is cautiously added. The mixture is stirred and cooled for 45 minutes; then the solid is collected, washed with water, and dried at 60° C. overnight. This solid is dissolved in 35 ml. of acetonitrile, filtered, and chilled overnight. The resulting solid is collected, washed with hexane, and dried, giving 3.7 g. of the desired product, m.p. 161°–163° C.

EXAMPLE 14

4-(p-Chloro-β-phenylcinnamamido)benzoic acid

To a suspension of 3.75 g. of hexane-washed sodium hydride (50% in oil) in 30 ml. of moist dimethylformamide is added dropwise a solution of 8.6 g. of 4-(2-phosphonoacetamido)benzoic acid, triethyl ester in 30 ml. of dimethylformamide. The mixture is stirred for 20 minutes, then 5.42 g. of 4-chlorobenzophenone are added, and this mixture is heated at 50°–70° C. for 2 hours. The mixture is cooled, 150 ml. of water is cautiously added, and stirring and cooling are continued for 30 minutes. The resulting solid is removed by filtration. The filtrate is acidified with concentrated hydrochloric acid, using ice bath cooling, and the resulting solid is collected, washed with water, and dried. This solid is then dissolved in 70 ml. of hot toluene, filtered, and the filtrate is chilled. The resulting solid is collected, washed with toluene, dried, dissolved in 40 ml. of hot acetonitrile, filtered, and chilled. The resulting solid is collected, washed with acetonitrile, and dried, giving 1.52 g. of the desired product, m.p. 220°–223° C.

EXAMPLE 15

4-(3,3-Diphenylacrylamido)benzoic acid

To a suspension of 7.2 g. of hexane-washed sodium hydride (50% in oil) in 30 ml. of moist dimethylformamide is added dropwise a solution of 17.15 g. of 4-(2-phosphonoacetamido)benzoic acid triethyl ester in 40 ml. of dimethylformamide. The mixture is stirred for 25 minutes, then 9.11 g. of benzophenone are added, and the mixture is heated at 60°–70° C. for 1.5 hours. The mixture is cooled, 250 ml. of water are cautiously added, and cooling and stirring are continued for 30 minutes. The mixture is filtered, the filtrate is cooled, acidified with concentrated hydrochloric acid, and the solid is collected and crystallized from 100 ml. of hot acetonitrile, giving 3.25 g. of the desired product as light yellow needles, m.p. 222°–224° C.

EXAMPLE 16 p-(3,3-Diphenylacrylamido)benzoic acid, ethyl ester

To a suspension of 1.44 g. of hexane-washed sodium hydride in 30 ml. of dry hexamethylphosphortriamide is added slowly a dry solution of 3.43 g. of 4-(2-phosphonoacetamido)benzoic acid triethyl ester in 30 ml. of hexamethylphosphortriamide. The mixture is stirred for 20 minutes, 1.82 g. of benzophenone are added, and the mixture is heated at 65° C. for 1.5 hours, then cooled and cautiously diluted with 250 ml. of water. This mixture is cooled in an ice bath and stirred for 30 minutes; then the solid is collected, washed with water, and dried. This solid is crystallized from 50 ml. of hot acetonitrile, giving 1.58 g. of the desired product, m.p. 166°–169° C.

EXAMPLE 17

4-[3,3-Di-(p-tolyl)acrylamido]benzoic acid, ethyl ester

To a solution of 5.76 g. of hexane-washed sodium hydride (50% in oil) in 40 ml. of dry hexamethylphosphortriamide is added, dropwise, a solution of 13.72 g. of 4-(2-phosphonoacetamido)benzoic acid triethyl ester in 100 ml. of dry hexamethylphosphortriamide. The mixture is stirred for 20 minutes, then 8.41 g. of 4,4'-dimethylbenzophenone are added. This mixture is heated at 70° C. for 4 hours, cooled, and cautiously diluted with water to a total volume of 1,300 ml. This mixture is extracted with two 400 ml. portions of ether. The ether extracts are combined, washed with water, dried over anhydrous magnesium sulfate, and evaporated to dryness. The residue is dissolved in 50 ml. of hot acetone, filtered, and the filtrate is diluted with hexane and cooled, giving a solid which is collected, washed with a mixture of acetone and hexane, and dried at 50° C., giving 5.0 g. of the desired product, m.p. 151°–154° C.

EXAMPLE 18

4-(p-Methyl-β-phenylcinnamamido)benzoic acid, ethyl ester

The proceduere of Example 16 is repeated, substituting 7.85 g. of 4-methylbenzophenone for the 4,4'-dimethylbenzophenone. The aqueous dilution of the cooled reaction mixture is extracted six times with ether giving 12.0 g. of a yellow oil. This oil is purified by preparative high pressure liquid chromatography, using a silica gel column, 12% ethylacetate in hexane as the solvent at a flow rate of 100 ml./minute. Fractions 7, 8, and 9 are combined, giving 5.8 g. of the desired product as a light yellow solid, m.p. 122°–124° C.

EXAMPLE 19

4-(p-Chloro-β-methylcinnamamido)benzoic acid, ethyl ester

To a solution of 4.32 g. of hexane-washed sodium hydride (50% in oil) in 30 ml. of hexamethylphosphortriamide is added, dropwise, a dry solution of 10.29 g. of 4-(2-phosphonoacetamido)benzoic acid, triethyl ester in 75 ml. of hexamethylphosphortriamide. The mixture is stirred 20 minutes, then 4.64 g. of 4'-chloroacetophenone are added, and this mixture is heated at 65°–70° C. for 4 hours. The mixture is cooled, cautiously diluted with 1 liter of water and extracted with three 250 ml. portions of ether. The ether extracts are combined, washed with saturated aqueous sodium chloride, dried over anhydrous magnesium sulfate, stirred with diatomaceous earth, and filtered. The filtrate is evaporated, and the residue is crystallized from acetonitrile. A 2.5 g. portion is recrystallized from a mixture of acetone and hexane, giving 1.66 g. of the desired product, m.p. 150°–152° C.

EXAMPLE 20

4-[3,3-Bis(p-chlorophenyl)propionamido]benzoic acid, sodium salt

A solution of 4.17 g. of sodium methoxide in 80 ml. of methanol is added to a mixture of 32.0 g. of 4-[3,3-bis(p-chlorophenyl)propionamido]benzoic acid in 500 ml. of methanol. The solution is filtered, then evaporated in vacuo, and dried at 50° C., giving 33.0 g. of the desired product as a white solid.

EXAMPLE 21

3,3-Bis(p-chlorophenyl-4'-cyanoacrylanilide

A mixture of 9.0 g. of bis(4-chlorophenyl)acrylic acid and 9.0 ml. of thionyl chloride is stirred for 24 hours and then evaporated to a yellow oil. This oil is dissolved in 50 ml. of dichloromethane and added to a stirred mixture of 3.54 g. of 4-aminobenzonitrile and 8.31 ml. of triethylamine in 50 ml. of dichloromethane. This solution is stirred under reflux for 4 hours and then evaporated. The residue is stirred with 250 ml. of boiling acetone, filtered, and the filtrate is concentrated to 100 ml. and allowed to cool. The solid is collected, dried, and recrystallized from 80 ml. of acetonitrile, giving 4.59 g. of the desired product as a light yellow solid, m.p. 228°–230° C.

EXAMPLE 22

4'-Acetyl-3,3-bis(p-chlorophenyl)acrylanilide

A 9.0 ml. portion of thionyl chloride is added to a solution of 9.0 g. of bis-(4-chlorophenyl)acrylic acid in 25 ml. of dichloromethane (exothermic). The solution is stirred for 4 hours under reflux and then evaporated to an oil. A solution of this oil in 50 ml. of dichloromethane is added in portions to a stirred solution of 4.05 g. of p-aminoacetophenone and 8.31 ml. of triethylamine in 50 ml. of dichloromethane (exothermic). This solution is stirred under reflux for 2 hours, then at room temperature overnight, and evaporated. The residue is stirred with 250 ml. of boiling acetone, filtered while hot, and the filtrate is concentrated to 100 ml., allowed to cool, and reflitered. This filtrate is evaporated, and the residue is crystallized from 220 ml. of acetonitrile. The resulting solid is again crystallized from 100 ml. of acetonitrile. Concentration of the filtrate to 40 ml. and chilling yields 320 mg. of the desired product as a light yellow solid, m.p. 213°–215° C.

EXAMPLE 23

4-[3,3-Bis(p-methoxyphenyl)acrylamido]benzoic acid, ethyl ester

To a suspension of 7.2 g. of hexane-washed sodium hydride (50% in oil) in 150 ml. of dry hexamethylphosphortriamide is added 22.3 g. of 4-(2-phosphonoacetamido)benzoic acid, triethyl ester, under argon. The mixture is stirred for 10 minutes, then 14.54 g. of 4,4'-dimethoxybenzophenone are added. The mixture is heated at 65°–70° C. for 5 hours, and allowed to stand overnight. The mixture is filtered through a celite pad. The pad is washed with water, then two 200 ml. portions of ether, then three 200 ml. portions of ethyl acetate. The ethyl acetate extracts are combined, dried over magnesium sulfate, and evaporated to dryness. The residue is crystallized from 50 ml. of hot acetonitrile giving 6.0 g. of solid. A 3.2 g. portion of this solid is purified by preparative high pressure liquid chromatography, using a silica gel column and the solvent system 30% ethyl acetate in hexane. Fractions 10–13 are combined, stripped to dryness, and the residue is dissolved in dichloromethane. This solution is filtered, hexane is added to the filtrate, and the solid is collected, washed with hexane, and dried, giving 1.7 g. of the desired product as a white solid, m.p. 156°–159° C.

EXAMPLE 24

4-(3,4-Dichlorophenyl-β-methylacrylamido)benzoic acid, ethyl ester

To a suspension of 4.32 g. of hexane-washed sodium hydride (50% in oil) in 150 ml. of dry hexamethylphosphortriamide under nitrogen is added 13.72 g. of 4-(2-phosphonoacetamido)benzoic acid triethyl ester. The mixture is stirred 20 minutes, then 5.67 g. of 3',4'-dichloroacetophenone are added. The mixture is heated at 65°–70° C. for 6 hours, cooled to 5° C., and cautiously diluted with 400 ml. of water. The mixture is filtered through a pad of celite. The pad is then washed with 250 ml. of ether followed by ethyl acetate. The ethyl acetate extract is dried, evaporated to dryness, and the residue is crystallized from acetonitrile, giving 3.2 g. of the desired product, m.p. 149°–150° C.

EXAMPLE 25

4-[3,3-Bis(p-bromophenyl)acrylamido]benzoic acid, ethyl ester

To a suspension of 0.9 g. of hexane-washed sodium hydride (50% in oil) in 40 ml. of dry hexamethylphosphortriamide under argon is added 2.7 g. of 4-(2-phosphonoacetamido)benzoic acid triethyl ester. The mixture is stirred for 5 minutes, then 2.0 g. of 4,4'-dibromobenzophenone are added. The mixture is heated at 70°–75° C. for 4 hours, cooled to 10° C., and cautiously diluted with 60 ml. of water. This mixture is stirred and cooled for ½ hour. The solid is collected, washed with water, and dried. A 1.5 g. portion is dissolved in 50 ml. of acetone, filtered, and hexane is added to the filtrate until turbid. The mixture is chilled, and the solid is collected, washed with hexane, and dried, giving 320 mg. of the desired product as a white solid, m.p. 207°–208° C.

EXAMPLE 26

4-(4-Chloro-3-nitro-β-phenylcinnamamido)benzoic acid, ethyl ester

To a suspension of 3.0 g. of hexane-washed sodium hydride (50% in oil) in 100 ml. of dry hexamethylphosphortriamide under argon is added 8.92 g. of 4-(2-phosphonoacetamido)benzoic acid triethyl ester. The mixture is stirred 5 minutes, then 5.23 g. of 4-chloro-3-nitrobenzophenone are added. This mixture is heated at 70° C. for 2 hours, cooled to 10° C., and cautiously diluted with 350 ml. of water and stirred for ½ hour. The mixture is filtered through a pad of celite. The pad is washed with water followed by 400 ml. of ethyl acetate. The ethyl acetate extract is washed with water, dried over anhydrous magnesium sulfate by preparative high pressure liquid chromatography on a silica gel column using ethyl acetate:hexane (25:75) as the solvent system and a flow rate of 100 ml./minute. Eighteen fractions are collected. The like fractions are pooled and stripped to dryness. A 2.71 g. portion of the residue is crystallized from 30 ml. of absolute ethanol giving three crops. The third crop comprises 120 mg. of the desired product.

EXAMPLE 27

4-[3,3-Bis(p-chlorophenyl)propionamido]benzoic acid, ethyl ester

A 30.2 g. portion of 4-[3,3-(p-chlorophenyl)acrylamido]benzoic acid, ethyl ester is hydrogenated as described in Example 3, giving 25.97 g. of the desired product, m.p. 152°-155° C.

The ethyl esters of certain of the compounds of this invention are converted to the corresponding acid derivatives by the procedures of Example 2, using either potassium hydroxide or sodium hydroxide as base. The products of this reaction are listed in Table II.

TABLE II

| Example | Starting Material | Product | M.P. °C. |
|---------|-------------------|---------|----------|
| 28 | 4-(p-Chlorohydrocinnamamido)-benzoic acid, ethyl ester | 4-(p-Chlorohydrocinnamamido)benzoic acid | 273–275 |
| 29 | 4-[3,3-Bis(p-chlorophenyl)-acrylamido]benzoic acid, ethyl ester | 4-[3,3-Bis(p-chlorophenyl)-acrylamido]benzoic acid | 258–259 |
| 30 | 4-[3,3-Bis(p-chlorophenyl)-propionamido]benzoic acid, ethyl ester | 4-[3,3-Bis(p-chlorophenyl)-propionamido]benzoic acid | 280–282 |
| 31 | 4-(p-Methoxycinnamamido)-benzoic acid, ethyl ester | 4-(p-Methoxycinnamamido)-benzoic acid | 289–291 |
| 32 | 3-[3,3-Bis(p-chlorophenyl)-acrylamido]benzoic acid, ethyl ester | 3 - [3,3-Bis(p-chlorophenyl)-acrylamido]benzoic acid | 211–215 |
| 33 | 2-[3,3-Bis(p-chlorophenyl)-acrylamido]benzoic acid, ethyl ester | 2-[3,3-Bis(p-chlorophenyl)-acrylamido]benzoic acid | 230–232 |
| 34 | 4-[3,3-Bis(p-fluorophenyl)-acrylamido]benzoic acid, ethyl ester | 4-[3,3-Bis(p-fluorophenyl)-acrylamido]benzoic acid | 245–247 |
| 35 | 4-(p-Methyl-$\beta$-phenylcinnamido)benzoic acid, ethyl ester | 4-(p-Methyl-$\beta$-phenylcinnamamido)benzoic acid | 221–223 |
| 36 | 4-(p-Chloro-$\beta$-methylcinnamamido)benzoic acid, ethyl ester | 4-(p-Chloro-$\beta$-methylcinnamamido)benzoic acid | 273–276 |
| 37 | 4-[3,3-Di-(p-tolyl)acrylamido]-benzoic acid, ethyl ester | 4-[3,3-Di-(p-tolyl)acrylamido]benzoic acid | 238–240 |
| 38 | 4-[3,3-Bis(p-methoxyphenyl)-acrylamido]benzoic acid, ethyl ester | 4-[3,3-Bis(p-methoxyphenyl)acrylamido]benzoic acid | 237–239 |
| 39 | 4-[3,3-Bis(p-bromophenyl)-acrylamido]benzoic acid, ethyl ester | 4-[3,3-Bis(p-bromophenyl)-acrylamido]benzoic acid | 259–261 |

EXAMPLE 40

4-[6-(p-Chlorophenyl)hexanamido]benzoic acid

To a solution of 101 g. of ethyl adipate in 500 ml. of benzene is slowly added 120 ml. of thionylchloride. The mixture is refluxed for 4.5 hours, cooled, and evaporated. The residue is evaporated three times from 500 ml. of benzene, giving 113 g. of ethyl adipoyl chloride as a yellow liquid.

A solution comprising 155 g. of aluminum chloride in 200 ml. of tetrachloroethane and 77 ml. of chlorobenzene is cooled to 3° C. in an ice bath. The 113 g. of ethyl adipoyl chloride is added slowly over a period of 3 hours, washing the oil in with small portions of tetrachloroethane and keeping the temperature below 5° C. The mixture is refrigerated overnight, then warmed to 50° C. into 1.5 liters of ice and water containing 200 ml. of 37% hydrochloric acid. The oil is drawn off, and the aqueous layer is washed with two 500 ml. portions of ether. The oil and ether extracts are combined, washed with water, then brine, dried, and evaporated, giving 159.1 g. of ethyl 5-(p-chlorobenzoyl)valerate.

To a solution of the 159 g. of the valerate in 400 ml. of ethanol is slowly added 80 g. of 85% potassium hydroxide. The mixture is allowed to stand 1/5 hour, 100 ml. of water are added, and the solution is stirred at reflux for 2 hours. The solution is cooled, the ethanol is evaporated, and the residue is dissolved in 1 liter of water, adjusted to pH 1 with 37% hydrochloric acid, and the solid is collected. Two crystallizations from ethanol give 69.5 g. of 5-(p-chlorobenzoyl)valeric acid.

A 55 g. portion of zinc is placed in a flask. To this is added 5.4 g. of mercuric chloride, 90 ml. of water, and 3 ml. of concentrated hydrochloric acid. The mixture is stirred for 5 minutes, and the solution is decanted. To this solution is sequentially added 35 ml. of water, 80 ml. of 37% hydrochloric acid, 45 ml. of toluene, and 35 g. of 5-p-(chlorobenzoyl)valeric acid. The mixture is stirred at reflux for 24 hours with the addition of 25 ml. portions of 37% hydrochloric acid after 6, 12, and 18 hours. The reaction is cooled and diluted with 100 ml. of water. The organic layer is separated and saved. The aqueous layer is extracted with two 100 ml. portions of ether. The organic layers are combined, dried, and condensed to an orange oil. This oil is distilled through a Kugelrohr apparatus. The distillate is dissolved in 100 ml. of ethanol, 500 mg. of 10% palladium on carbon are added, and the mixture is hydrogenated at 40 p.s.i. for one hour in a Parr apparatus. The catalyst is removed by filtration and the filtrate is evaporated, giving 25.2 g. of 6-(p-chlorophenyl)hexanoic acid.

A solution of 15 g. of 6-(p-chlorophenyl)hexanoic acid and 14 ml. of thionyl chloride in 200 ml. of benzene is refluxed for 6 hours, then cooled, the solvent is evaporated and the residue dissolved in benzene, and the solution is evaporated to yield 16.7 g. of 6-(p-chlorophenyl)hexanoic acid chloride as an oil.

To a solution of 11.7 g. of this acid chloride in 100 ml. of dichloromethane is added a solution of 15.8 g. of benzocaine in 100 ml. of dichloromethane. The mixture is stirred for 4 hours, then washed with 100 ml. of 10% hydrochloric acid, 100 ml. of water, dried, filtered through magnesol, and evaporated to yield a solid. This solid is crystallized from 150 ml. of toluene, giving 14.98 g. of 4-6-(p-chlorophenyl)hexanamidobenzoic acid, ethyl ester.

This ester (7.61 g.) is reduced to the desired product by the procedure of Example 2, giving 5.54 g. of white crystals, m.p. 218°-220° C.

EXAMPLE 41

4-[5,5-Bis(p-chlorophenyl)-2,4-pentadienamido]benzoic acid, ethyl ester

A slurry of 22 g. of hexane-washed sodium hydride (50% in oil) in 500 g. of hexamethylphosphortriamide is stirred at 32° C. while 96.5 g. of 4,4'-dichlorobenzophenone and a solution of 125 g. of triethyl 4-phosphonocrotonate in 500 ml. of hexamethylphosphortriamide are added. After one hour the temperature is raised to 75° C., and stirring is continued overnight. The mixture is cooled, diluted with 500 ml. of water, and extracted with three 500 ml. portions of ether. The ether extracts are combined, dried over magnesium sulfate, and concentrated to a solid. This solid is dissolved in 300 ml. of ether and chromatographed on 600 g. of silica gell, eluting eith 2 liters of ether. The ether is concentrated in vacuo to an oil which is triturated with 100 ml. of hexane, giving 59.1 g. of ethyl 5,5-bis(p-chlorophenyl)pent-2,4-dienoate.

To a suspension of 20 g. of the above ester in 50 ml. of ethanol is added a solution of 3.8 g. of potassium hydroxide in 150 ml. of water. The mixture is refluxed for 6 hours, filtered while hot, acidified with 7 ml. of concentrated hydrochloric acid, and then cooled in ice. The solid is collected, washed with water, and dried, giving 10.0 g. of 5,5-bis(p-chlorophenyl)-2,4-pentadienoic acid.

A mixture of 13.0 g. of the above acid and 35 ml. of thionyl chloride is stirred overnight, evaporated to dryness, and concentrated twice from 50 ml. of dichloromethane. The solid is dissolved in 100 ml. of dichloromethane, and a mixture of 6.8 g. of ethyl p-aminobenzoate, 100 ml. of dichloromethane, and 11 ml. of triethylamine is added dropwise over 30 minutes. The solution is stirred overnight, filtered, and concentrated in vacuo. The residue is dissolved in acetone, heated to boiling, filtered, cooled, and refiltered. This filtrate is concentrated to a solid. A 10.0 g. portion of this solid is chromatographed on a silica gel, eluting with dichloromethane, and collecting 500 ml. fractions. Fractions 15–20 are combined and recrystallized from dichloromethane and then dried giving a white solid. This solid is recrystallized several times from ether, giving the desired product as an off-white solid, m.p. 216°–218° C.

EXAMPLE 42

4-[5,5-Bis(p-chlorophenyl)-2,4-pentadienamido]benzoic acid

A mixture of 4.0 g. of p-[5,5-bis(p-chlorophenyl)-2,4-pentadienamido]benzoic acid, ethyl ester, 40 ml. of ethanol, and 10 ml. of 1N sodium hydroxide is heated at reflux for 4 hours, filtered while hot, 15 ml. of 1N hydrochloric acid are added, and the mixture is cooled in ice. The solid is collected, washed with water, dried and recrystallized from ethanol, giving 3.1 g. of the desired product, m.p. 273°–276° C.

EXAMPLE 43

4-[2,2-Bis(p-chlorophenyl)acetamido]benzoic acid, ethyl ester

A mixture of 49.5 g. of 1,1'-(2,2,2-trichloroethylidene)bis[p-chlorobenzene], 400 ml. of diethylene glycol, and a solution of 63 g. of potassium hydroxide in 35 ml. of water is heated at reflux for 6 hours, then cooled, and poured slowly into 1 liter of cold water with stirring. The solution is filtered, and the filtrate is warmed to 90° C. and stirred with 2 g. of charcoal for 10 minutes. The solution is filtered, made acidic with 55 ml. of concentrated sulfuric acid, and refrigerated for 6 hours. The solid is collected and crystallized from ethanol:water (100:75), giving 28.0 g. of bis(p-chlorophenyl)acetic acid.

To a stirred solution of 23.55 g. of bis(p-chlorophenyl)acetic acid in 250 ml. of benzene is added dropwise 33.1 g. of sulfonyl chloride. The mixture is refluxed 5 hours, the solvent is evaporated, and the residue is evaporated from three 250 ml. portions of benzene, giving 26.06 g. of bis(p-chlorophenyl)acetyl chloride as an oil. To this oil is added a solution of 27.7 g. of benzocaine. The mixture is stirred overnight, filtered, washed with 200 ml. each of 10% hydrochloric acid, saturated sodium bicarbonate solution, water, and brine, dried over magnesium sulfate, and evaporated. The residue is crystallized twice from 200 ml. of ethanol, giving 25.76 g. of the desired product as colorless needles, m.p. 171°–172° C.

EXAMPLE 44

4-[2,2-Bis(p-chlorophenyl)acetamido]benzoic acid

A mixture of 6.0 g. of p-[2,2-bis(p-chlorophenyl)acetamido]benzoic acid, ethyl ester, 920 mg. of potassium hydroxide, and 50 ml. of 95% ethanol is stirred at 75° C. for 9 hours, cooled, diluted with 100 ml. of water, and the pH is adjusted to 2.0 with 37% hydrochloric acid. The precipitate is collected, washed with water, dried and recrystallized from 100 ml. of ethanol, giving 2.78 g. of the desired product as colorless crystals, m.p. 272°–274° C.

EXAMPLE 45

4-[6-(p-Chlorophenyl)hexanamido]benzoic acid, ethyl ester

A mixture of 150 g. of aluminum chloride, 200 ml. of dichloromethane, and 84.2 g. of chlorobenzene is cooled in an ice bath to 30° C.; then 108.1 g. of ethyl adipoyl chloride are added dropwise with stirring, maintaining the temperature at less than 50° C. The mixture is refrigerated overnight, then warmed slowly to 50° C., and poured slowly into a stirred mixture of 200 ml. of 37% hydrochloric acid and 1,200 g. of crushed ice. When the ice melts, the organic layer is separated and saved. The aqueous layer is extracted with two 500 ml. portions of ether. The ether extracts are combined with the original organic layer, washed with 300 ml. of water, then 500 ml. of brine, dried over magnesium sulfate, and evaporated to a solid. This solid is recrystallized from 300 ml. of methylcyclohexane, giving 78.4 g. of 5-(p-chlorobenzoyl)valeric acid, ethyl ester.

A 139.3 g. portion of 5-chlorobenzoyl valeric acid, ethyl ester (prepared as described above) is dissolved in 400 ml. of 95% ethanol. An 80 g. portion of potassium hydroxide and 75 ml. of water are added, and the mixture is refluxed for 3 hours. The solution is cooled, poured into 1.2 liters of water, and the pH is adjusted to 1 with 37% hydrochloric acid. The solid is collected, dried, and crystallized from 400 ml. of toluene, giving 70.0 g. of 5-p-chlorobenzoyl valeric acid.

A mixture of 55 g. of mossy zinc, 5.4 g. of mercuric chloride, 90 ml. of water, and 3 ml. of concentrated hydrochloric acid is stirred for 5 minutes, and the solution is decanted. To the residue is suquentially added 35 ml. of water, 80 ml. of 37% hydrochloric acid, 45 ml. of toluene, and 30.0 g. of 5-p-chlorobenzoylvalerica cid. This mixture is refluxed at 115° C. for 28 hours, with the addition of 25 ml. of concentrated hydrochloric acid at 6 hour intervals. The solution is cooled, diluted with 100 ml. of water, and the organic layer is separated and saved. The aqueous layer is extracted with three 100 ml. portions of ether. The ether extracts and organic layer are combined, washed with 100 ml. of water, then 100 ml. of brine, dried over magnesium sulfate, and evaporated to an oil. This oil is distilled on a Kugelrohr apparatus collecting the fraction that boils at 160°–170° C. (60 mm.), giving 22.0 g. of 6-(p-chlorophenyl)hexanoic acid as an oil. To a solution of 19.0 g. of this oil in 200 ml. of benzene is added dropwise 33.1 g. of sulfonyl chloride. The mixture is refluxed 5 hours, cooled, and evaporated three times from 250 ml. of benzene, to yield 21.09 g. of brown liquid. This liquid is dissolved in 200 ml. of dichloromethane, and a solution of 28.4 g. of benzocaine in 200 ml. of dichloromethane is added, and the mixture is stirred overnight. The mixture is filtered, and the filtrate is extrcted with 100 ml. of 10% hydrochloric acid, 100 ml. of saturated sodium bicarbonate solution, and 100 ml. of brine; then it is dried over magnesium sulfate and evaporated to a solid. The solid is boiled in 400 ml. of toluene, treated with 1 g. of charcoal, filtered, and boiled down, giving 23.0 g. of crystalline solid. A 4.1 g. portion of this solid, 100 mg. of 10% palladium on carbon, and 50 ml. of ethyl acetate are hydrogenated in a Parr apparatus giving, after crystallization from toluene, 3.81 g. of the desired product as colorless crystals, m.p. 107°–108° C.

The final catalytic hydrogenation is necessary to convert ethyl p-[6-(p-chlorophenyl)hex-5-enamido]benzoate, an impurity present in the product, to the desired product. This impurity arises from 6-(p-chlorophenyl)-hex-5-enoic acid, a by-product formed during the preparation of the intermediate 6-(p-chlorophenyl)hexanoic acid, and thus the catalytic hydrogenation may alternatively be performed on the intermediate itself.

EXAMPLE 46

3,3-Bis(4-methoxyphenyl)propionic acid

A mixture of 10 g. of p-methoxycinnamic acid and 100 ml. of 85% phosphoric acid is stirred at approximately B 75° C. while 6.07 g. of anisole is added for about 24 hours thereafter. The mixture is allowed to cool, then is poured into ice water, and is filtered. The solid is crystallized from hexane-methylene chloride to yield 16.2 g. of 3,3-bis(4-methoxyphenyl)propionic acid as a white solid, m.p. 132°–134° C.

Amides prepared from 3,3-bis(4-methoxyphenyl)propionic acid by the method of Example 1 are shown in Table III.

TABLE III

| EXAMPLE | PRODUCT | M.P. °C. |
|---|---|---|
| 47 | N—Phenyl-3,3-bis(4-methoxyphenyl)propionamide | 168–171 |
| 48 | N—(p-Chlorophenyl)-3,3-bis(4-methoxyphenyl)propionamide | 165–168 |
| 49 | N—(p-Bromophenyl)-3,3-bis(4-methoxyphenyl)propionamide | 171–173 |
| 50 | N—(p-Fluorophenyl)-3,3-bis(4-methoxyphenyl)propionamide | 154–156 |
| 51 | N—(p-Nitrophenyl)-3,3-bis(4-methoxyphenyl)propionamide | 119–122 |
| 52 | N—(p-Tolyl)-3,3-bis(4-methoxyphenyl)propionamide | 157–159 |
| 53 | N—(p-Methoxyphenyl)-3,3-bis(4-methoxyphenyl)propionamide | 203–205 |
| 54 | N—(p-Cyanophenyl)-3,3-bis(4-methoxyphenyl)propionamide | 144–145 |
| 55 | N—(p-Trifluoromethylphenyl)-3,3-bis(4-methoxyphenyl)propionamide | 171–173 |
| 56 | 4'-[3,3-Bis(4-methoxyphenyl)propionamido]acetophenone | 158–161 |
| 57 | Ethyl 4'-[3,3-bis(4-methoxyphenyl)propionamido]benzoate | 150–151 |
| 58 | 4'-[3,3-Bis(4-methoxyphenyl)propionamido]benzoic acid | 250 dec |

EXAMPLE 59

3,3-Bis(p-tolyl)propionic acid

A suspension of 1.6 g. of lithium aluminum hydride and 250 ml. of ether is stirred at reflux while 30 g. of 4,4'-dimethylbenzophenone is added and for 4 hours thereafter. Unreacted hydride is decomposed by the addition of aqueous sodium hydroxide solution, and the mixture is filtered. The filtrate is extracted with ether, and the extract is dried and evaporated to yield 28.1 g. of 4,4'-dimethylbenzhydrol, m.p. 69°–70° C.

An ether solution of the 28.1 g. of 4,4'-dimethylbenzhydrol is treated with anhydrous hydrogen chloride and stirred at about 25° C. Evaporation followed by crystallization from petroleum ether affords 24.4 g. of 4,4'-dimethylbenzhydryl chloride as a white solid.

A mixture of 11.5 g. of sodium hydride (60% in mineral oil) and 250 ml. of tetrahydrofuran is treated with a solution of 38.4 g. of diethyl malonate in 100 ml. of tetrahydrofuran followed by 16.0 g. of sodium iodide and 25.0 g. of 4,4'-dimethylbenzhydryl chloride. The mixture is stirred for 24 hours at 25° C. and then poured into ice and extracted with ether. The dried extract is evaporated, and the residue is crystallized from hexanemethylene chloride to yield 26.1 g. of diethyl 2-(4,4'-dimethylbenzhydryl)malonate, m.p. 74°–75° C.

A mixture of 2.95 g. of this diester, 10 ml. of ethanol, and 10 ml. of 5N sodium hydroxide solution is stirred under reflux for 3 hours and evaporated. A solution of the residue in water is acidified and filtered to yield 2.35 g. of 2-(4,4'-dimethylbenzhydryl)malonic acid, m.p. 188°–191° C.

A 2.2 g. sample of this diacid is heated until it melts; the heating is continued for 5 minutes thereafter. The material is crystallized from ethanol to yield 1.51 g. of 3,3-bis(p-tolyl)propionic acid, m.p. 44°–46° C.

Amides prepared from 3,3-bis(p-tolyl)propionic acid by the method of Example 1 are shown in Table IV.

TABLE IV

| EXAMPLE | PRODUCT | M.P. °C. |
|---|---|---|
| 60 | N—Phenyl-3,3-bis(p-tolyl)propionamide | 143–146 |
| 61 | N—(p-Chlorophenyl)-3,3-bis(p-tolyl)propionamide | 153–155 |
| 62 | N—(p-Fluorophenyl)-3,3-bis(p-tolyl)propionamide | 131–134 |
| 63 | N—(p-Cyanophenyl)-3,3-bis(p-tolyl)propionamide | 163–166 |
| 64 | N—(p-Tolyl)-3,3-bis(p-tolyl)propionamide | 180–183 |
| 65 | Ethyl 4'-[3,3-bis(4-methylphenyl)propionamido]benzoate | 164–166 |
| 66 | N—(p-Trifluoromethylphenyl)-3,3-bis(p-tolyl)propionamide | 157–160 |

EXAMPLE 67

3,3-Bis(4-chlorophenyl)propionic acid

A 38.4 g. quantity of sodium hydride (50% in mineral oil) is washed with hexane to remove the mineral oil and then stirred with 2.0 l. of tetrahydrofuran at 10° C. while 158 ml. of triethyl phosphonoacetate is added during 15 minutes followed by 167 g. of 4,4'-dichlorobenzophenone. The solution is then stirred at 25° C. for 20 hours. The mixture is evaporated, and the residue partitioned between methylene chloride and water. The organic layer is dried and evaporated to yield 201 g. of ethyl 3,3-bis(4-chlorophenyl)acrylate, m.p. 58°-61° C.

A solution of 32.1 g. of this ester in 250 ml. of cyclohexane is treated with 1.6 g. of platinum oxide and shaken under 40 p.s.i. of hydrogen for about 6 hours. The mixture is filtered and the filtrate evaporated. The residue is crystallized from ethanol to yield 22.8 g. of ethyl 3,3-bis(4-chlorophenyl)propionate, m.p. 48°-52° C.

A solution of 25.0 g. of this ester and 9.6 g. of

A solution of 25.0 g. of this ester and 9.6 g. of potassium hydroxide in 200 ml. of 95% aqueous ethanol is stirred under reflux for 4 hours, allowed to cool, and poured into ice water. The mixture is acidified with 6N hydrochloric acid and filtered. The solid is recrystallized from acetonitrile to yield 22.0 g. of 3,3-bis(4-chlorophenyl)propionic acid as a white solid, m.p. 190°-193° C.

Amides prepared from 3,3-bis(p-chlorophenyl)propionic acid by the method of Example 1 are shown in Table V.

TABLE V

| EXAMPLE | PRODUCT | M.P. °C. |
|---|---|---|
| 68 | N—Phenyl-3,3-bis(p-chlorophenyl)propionamide | 207-209 |
| 69 | N—(4-Fluorophenyl)-3,3-bis(p-chlorophenyl)propionamide | 193-196 |
| 70 | N—(4-Tolyl)-3,3-bis(p-chlorophenyl)propionamide | 233-235 |
| 71 | N—(4-Cyanophenyl)-3,3-bis(p-chlorophenyl)propionamide | 190—192 |
| 72 | N—(4-Acetylphenyl)-3,3-bis(p-chlorophenyl)propionamide | 146-148 |
| 73 | N—(4-Trifluoromethylphenyl)-3,3-bis(p-chlorophenyl)propionamide | 181-184 |

No effort has been made to optimize the yields obtained in the aforementioned Examples.

We claim:

1. A compound of the formula:

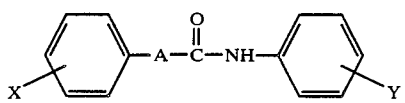

wherein A is a moiety of the formulae:

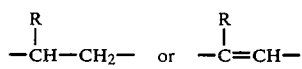

wherein R is alkyl ($C_1$–$C_4$) or phenyl substituted with one or more substituents selected independently of X from the group consisting of those from which X is selected; X represents one or more substituents independently selected from the group consisting of hydrogen, ($C_1$–$C_4$)alkyl, hydroxy, ($C_1$–$C_4$)alkoxy, halo, and nitro; Y represents one or more substituents independently selected from the group consisting of hydrogen, ($C_1$–$C_4$)alkyl, hydroxy, ($C_1$–$C_4$)alkoxy, halo, trifluoromethyl, nitro, amino, acetamido, acetyl, formyl, cyano, carboxy, ($C_1$–$C_4$)carboalkoxy, carboxamido, sulfonamido, —$CO_2CH_2CO_2C_2H_5$, —$CO_2CH_2CO_2CH_3$, and —$CO_2CH_2CO_2H$; and the pharmaceutically acceptable salts thereof.

2. A compound according to claim 1 wherein Y is carboalkoxy.

3. A compound according to claim 1 wherein Y is carboxy and the alkali metal salts thereof.

4. A compound according to claim 1 wherein Y is hydrogen.

5. The compound according to claim 1; 4-[3,3-bis-(p-chlorophenyl)propionamido]benzoic acid.

6. The compound according to claim 1; 4-[3,3-bis-p-tolyl)propionamido]benzoic acid.

7. The compound according to claim 1; 4-[3,3-bis-(p-methoxyphenyl)propionamido]benzoic acid.

8. The compound according to claim 1; ethyl 4-[3,3-bis-(p-chlorophenyl)propionamido]benzoate.

9. The compound according to claim 1; ethyl 4-[3,3-bis-(p-tolyl)propionamido]benzoate.

10. The compound according to claim 1; ethyl 4-[3,3-bis-(p-methoxyphenyl)propionamido]benzoate.

11. The compound according to claim 1; sodium 4-[3,3-bis-(p-chlorophenyl)propionamido]benzoate.

12. The compound according to claim 1; sodium 4-[3,3-bis-(p-tolyl)propionamido]benzoate.

13. The compound according to claim 1; sodium 4-[3,3-bis-(p-methoxyphenyl)propionamido]benzoate.

14. The compound according to claim 1; 4-[3,3-bis-(p-chlorophenyl)acrylamido]benzoic acid.

15. The compound according to claim 1; ethyl 4-[3,3-bis-(p-chlorophenyl)acrylamido]benzoate.

16. The compound according to claim 1; sodium 4-[3,3-bis-(p-chloropheyl)acrylamido]benzoate.

17. The compound according to claim 1; ethyl 4-[3,3-bis-(p-tolyl)acrylamido]benzoate.

18. The compound according to claim 1; ethyl 4-[3,3-bis-(p-methoxyphenyl)acrylamido]benzoate.

19. The compound according to claim 1; 3,3-bis-(p-chlorophenyl)acrylanilide.

20. The compound according to claim 1; 3,3-bis-(p-tolyl)acrylanilide.

21. The compound according to claim 1; 3,3-bis-(p-methoxyphenyl)acrylanilide.

22. The compound according to claim 1; 3,3-bis-(p-chlorophenyl)propionanilide.

23. The compound according to claim 1; 3,3-bis-(p-tolyl)propionanilide.

24. The compound according to claim 1; 3,3-bis-(p-methoxyphenyl)propionanilide.

25. The compound according to claim 1; N-phenyl-3,3-bis(4-methoxyphenyl)propionamide.

26. The compound according to claim 1; N-(p-chlorophenyl)-3,3-bis(4-methoxyphenyl)propionamide.

27. The compound according to claim 1; N-(p-bromophenyl)-3,3-bis(4-methoxyphenyl)propionamide.

28. The compound according to claim 1; N-(p-fluorophenyl)-3,3-bis(4-methoxyphenyl)propionamide.

29. The compound according to claim 1; N-(p-nitrophenyl)-3,3-bis(4-methoxyphenyl)propionamide.

30. The compound according to claim 1; N-(p-tolyl)-3,3-bis(4-methoxyphenyl)propionamide.

31. The compound according to claim 1; N-(p-methoxyphenyl)-3,3-bis(4-methoxyphenyl)propionamide.

32. The compound according to claim 1; N-(p-cyanophenyl)-3,3-bis(4-methoxyphenyl)propionamide.

33. The compound according to claim 1; N-(p-trifluoromethylphenyl)-3,3-bis(4-methoxyphenyl)propionamide.

34. The compound according to claim 1; 4'-[3,3-bis(4-methoxyphenyl)propionamido]acetophenone.

35. The compound according to claim 1; ethyl 4'-[3,3-bis(4-methoxyphenyl)propionamido]benzoate.

36. The compound according to claim 1 4'-[3,3-bis(4-methoxyphenyl)propionamido]benzoic acid.

37. The compound according to claim 1; N-phenyl-3,3-bis(p-tolyl)propionamide.

38. The compound according to claim 1; N-(p-chlorophenyl)-3,3-bis(p-tolyl)propionamide.

39. The compound according to claim 1; N-(p-fluorophenyl)-3,3-bis(p-tolyl)propionamide.

40. The compound according to claim 1; N-(p-cyanophenyl)-3,3-bis(p-tolyl)propionamide.

41. The compound according to claim 1; N-(p-tolyl)-3,3-bis(p-tolyl)propionamide.

42. The compound according to claim 1; ethyl 4'-[3,3-bis(4-methylphenyl)propionamido]benzoate.

43. The compound according to claim 1; N-(p-trifluoromethylphenyl)-3,3-bis(p-tolyl)propionamide.

44. The compound according to claim 1; N-phenyl-3,3-bis(p-chlorophenyl)propionamide.

45. The compound according to claim 1; N-(4-fluorophenyl)-3,3-bis(p-chlorophenyl)propionamide.

46. The compound according to claim 1; N-(4-tolyl)-3,3-bis(p-chlorophenyl)propionamide.

47. The compound according to claim 1; N-(4-cyanophenyl)-3,3-bis(p-chlorophenyl)propionamide.

48. The compound according to claim 1; N-(4-acetylphenyl)-3,3-bis(p-chlorophenyl)propionamide.

49. The compound according to claim 1; N-(4-trifluoromethylphenyl)-3,3-bis-(p-chlorophenyl)propionamide.

* * * * *